(12) United States Patent
Takeuchi et al.

(10) Patent No.: US 8,853,130 B2
(45) Date of Patent: Oct. 7, 2014

(54) YIELD ENHANCING AGENT FOR HARVESTING PART OF CROP

(75) Inventors: Yasutomo Takeuchi, Utsunomiya (JP); Shigeyuki Funada, Satte (JP)

(73) Assignee: Cosmo Oil Co., Ltd., Tokyo (JP)

( * ) Notice: Subject to any disclaimer, the term of this patent is extended or adjusted under 35 U.S.C. 154(b) by 255 days.

(21) Appl. No.: 12/720,723

(22) Filed: Mar. 10, 2010

(65) Prior Publication Data

US 2010/0234231 A1    Sep. 16, 2010

(30) Foreign Application Priority Data

Mar. 11, 2009   (JP) ................................. 2009-057313

(51) Int. Cl.
*A01N 33/00* (2006.01)
*A01N 25/00* (2006.01)
*A01N 33/04* (2006.01)
*A01N 33/08* (2006.01)

(52) U.S. Cl.
CPC ................. *A01N 25/00* (2013.01); *A01N 33/04* (2013.01); *A01N 33/08* (2013.01); *A01B 37/44* (2013.01)
USPC .......................................... 504/326; 504/320

(58) Field of Classification Search
CPC ............................... A01N 33/08; A01N 33/04
USPC .................................................. 504/326, 320
See application file for complete search history.

(56) References Cited

U.S. PATENT DOCUMENTS 5,298,482 A * 3/1994 Tanaka et al. .................. 504/320
5,661,111 A * 8/1997 Kuramochi et al. ........... 504/284
2008/0280765 A1   11/2008 Itai et al.

FOREIGN PATENT DOCUMENTS

| JP | 07-053487 A | 2/1995 |
|---|---|---|
| JP | 08-056491 A | 3/1996 |
| JP | 08-225408 A | 9/1996 |
| JP | 09-000069 A | 1/1997 |
| JP | 2007-252248 A | 10/2007 |
| WO | 2007-086372 A1 | 8/2007 |
| WO | 2008/018273 A1 | 2/2008 |

OTHER PUBLICATIONS

Zhang et al. (Separation of Uniconazole by Enantiomers Capillary Electrophoresis with Dual Cyclodextrin Systems, Canadian Journal of Analytical Sciences and Spectroscopy, Apr. 10, 2004).*
Iwai Kazuya, et al.; "Recovering effect of trace-element fertilizer containing 5-aminolevulinic acid (ALA) on the growth-delay of sugar beete seedlings caused by uniconazoole" Proceedings of Japanese Society for Chemical Regulation of Plants; No. 38, p. 71.
Office Action dated Jan. 30, 2013, issued by the State Intellectual Property Office of the People's Republic of China in Chinese Patent Application No. 201010130580.8.
Communication dated Dec. 11, 2012, issued by the Japanese Patent Office in Japanese application No. 2009-057313.
Notification of Fourth Office Action dated Apr. 9, 2014, issued by the State Intellectual Property Office of the People's Republic of China in Chinese Application No. 201010130580.8.

* cited by examiner

*Primary Examiner* — Rebecca Prouty
*Assistant Examiner* — Danielle Sullivan
(74) *Attorney, Agent, or Firm* — Sughrue Mion, PLLC

(57) ABSTRACT

A means for enhancing the yield of a harvesting part of a crop is provided. A yield enhancing agent for a harvesting part selected from the group consisting of seed, fruit, hypocotyl, root and stem in a crop, the yield enhancing agent comprising: 5-aminolevulic acid or a derivative thereof represented by the following formula (1), or a salt thereof; and a gibberellin biosynthesis inhibitor: $R^2R^1NCH_2COCH_2CH_2COR^3$ (1), wherein $R^1$ and $R^2$ each independently represent a hydrogen atom, an alkyl group, an acyl group, an alkoxycarbonyl group, an aryl group or an aralkyl group; and $R^3$ represents a hydroxyl group, an alkoxy group, an acyloxy group, an alkoxycarbonyloxy group, an aryloxy group, an aralkyloxy group or an amino group, wherein the yield enhancing agent is an agent to be applied at the time when the harvesting part of the crop becomes enlarged.

3 Claims, No Drawings

YIELD ENHANCING AGENT FOR HARVESTING PART OF CROP

BACKGROUND OF THE INVENTION

1. Field of the Invention

The present invention relates to a yield enhancing agent which increases the yield of a harvesting part of crop.

2. Background Art

Methods for enhancing the yield of crops include a method of treating with triacontanol during a tillering stage of rice (Chemical regulation of plants, 28 (1), 79, (1993)), a method of subjecting seeds of beans to an immersion treatment in carpropamide (JP-A-2001-247417), and the like.

However, the yield enhancing techniques as described above require restriction or management of the amount of practical use in consideration of the chemical characteristics of the active ingredients, or strict establishment of the conditions for actual use or combined use with other components upon stably increasing the yield of crops.

On the other hand, 5-aminolevulic acid, derivatives thereof, or salts of the acid or the derivatives exhibit an enhancement of photosynthetic activity, an enhancement of $CO_2$ absorption capacity, a respiratory suppressing action, a chlorophyll content increasing action, and an excellent growth promoting action. As a result, the compounds are known to be excellent in the effects of promotion of rooting, prevention of falling down, enhancement of yield, enhancement of cold resistance, retainment of freshness, enhancement of green color, maintenance of green color, retainment of good seedling, growth promotion of organs, increase of tillering number, reduction of the time required for growth, alleviation of harmful effects of chemicals, and enhancement of survival in cuttage or the like (JP-A-4-338305).

Furthermore, it is reported that when sugar beet seedlings are treated with uniconazole P, which is an inhibitor of gibberellin biosynthesis, and then treated with 5-aminolevulic acid, a derivative thereof or a salt thereof, healthy growth of sugar beet seedlings can be carried out (Proceedings of Japanese Society for Chemical Regulation of Plants, No. 38, p. 71). This is a technology in which the problem that the effect of uniconazole P used to prevent turion in sugar beet seedlings is sustained so that growth stagnation such as reduction of the dry weight occurs, is solved by treating with 5-aminolevulic acid after 15 days of uniconazole P treatment, and thereby increasing the dry weight with the growth promoting effect of 5-aminolevulic acid, so as to return to healthy growth.

SUMMARY OF THE INVENTION

Harvest of crops is determined by the multiplication product of the conditions for growth of seedlings and the conditions for enlargement of the harvesting part (seed, fruit, hypocotyl, stem or root). For example, when the force originally possessed by the plant is defined as 100%, if the conditions for growth of seedlings are defined as 90%, and the conditions for enlargement of the harvesting part is 90%, the harvest amount is 90%×90% that is 81%. When suppression of turion is carried out by 5-aminolevulic acid, a derivative thereof or a salt of the acid or the derivative, and by a gibberellin biosynthesis inhibitor, there is an effect of maintaining the growth conditions for seedlings of normal years even under the growth conditions that are so poor that seedlings are in the state of turion. It is an effect such that, for example, while the growth conditions for seedlings of normal years is 90%, a decrease to 80% in the growth conditions for seedlings as a result of turion is returned to 90%. As a method for preventing turion of seedlings, there are available an inhibitor of gibberellin biosynthesis, a salting treatment of giving stress to the rhizosphere, and the like. However, the amount of harvest for those seedlings which have been prevented from turion becomes equivalent to the ordinary amount of harvest for the seedlings that are not in the state of turion. For example, when the conditions for enlargement of a harvest object is defined as 90% for normal years, prevention of turion maintains 90% without affecting the conditions for enlargement of the harvest object.

That is, prevention of turion and growth of healthy seedlings as described in the Non-Patent Document 2 allow recovery and enhancement of the growth conditions of seedlings, but when a comparison is made with the conditions of the same seedlings, the prevention of turion and growth of healthy seedlings do not affect the yield of the harvesting part.

Therefore, development of a means for enhancing the yield of the harvesting part of crops is desired.

There, the present inventors conducted an investigation on the development of a means for enhancing the yield of a harvesting part of crops, and found that when a gibberellin biosynthesis inhibitor, which suppresses extension, and 5-aminolevulic acid, a derivative thereof or a salt thereof, which has a growth promoting effect, is applied at the stage when enlargement of a harvesting part characteristic to each plant, such as seed, fruit, hypocotyl, stem or root is occurred, the conditions for enlargement of the harvesting part can be increased, and the yield is increased.

That is, the present invention is to provide a yield enhancing agent having the following constitution.

[1] A yield enhancing agent for a harvesting part selected from the group consisting of seed, fruit, hypocotyl, root and stem in a crop, the yield enhancing agent comprising: 5-aminolevulic acid or a derivative thereof represented by the following formula (1), or a salt thereof; and a gibberellin biosynthesis inhibitor:

$$R^2R^1NCH_2COCH_2CH_2COR^3 \qquad (1)$$

wherein $R^1$ and $R^2$ each independently represent a hydrogen atom, an alkyl group, an acyl group, an alkoxycarbonyl group, an aryl group or an aralkyl group; and $R^3$ represents a hydroxyl group, an alkoxy group, an acyloxy group, an alkoxycarbonyloxy group, an aryloxy group, an aralkyloxy group or an amino group, wherein the yield enhancing agent is an agent to be applied at the time when the harvesting part of the crop becomes enlarged.

[2] The yield enhancing agent according to [1] above, wherein the gibberellin biosynthesis inhibitor is at least one selected from the group consisting of uniconazole P, prohexadione calcium salt, and salts or isomers thereof.

[3] The yield enhancing agent according to [1] or [2] above, wherein the crop is a Gramineae, a Cruciferae or a Compositae.

[4] The yield enhancing agent according to [3] above, wherein the crop of Gramineae, Cruciferae or Compositae is rice, barley, radish or sunflower.

[5] The yield enhancing agent according to any one of [1] to [4] above, which is an agent for applying simultaneously 5-aminolevulic acid or a derivative thereof, or a salt thereof and a gibberellin biosynthesis inhibitor.

[6] A method for enhancing a yield of a harvesting part selected from the group consisting of seed, fruit, hypocotyl, root and stem in a crop, wherein the method comprises applying 5-aminolevulic acid or a derivative thereof represented by the following formula (1), or a salt thereof and a gibberellin biosynthesis inhibitor at the time when the harvesting part of the crop becomes enlarged:

$$R^2R^1NCH_2COCH_2CH_2COR^3 \qquad (1)$$

wherein $R^1$ and $R^2$ each independently represent a hydrogen atom, an alkyl group, an acyl group, an alkoxycarbonyl group, an aryl group or an aralkyl group; and $R^3$ represents a hydroxyl group, an alkoxy group, an acyloxy group, an alkoxycarbonyloxy group, an aryloxy group, an aralkyloxy group or an amino group.

[7] The method for enhancing a yield according to [6] above, wherein the 5-aminolevulic acid or a derivative thereof, or a salt thereof and the gibberellin biosynthesis inhibitor are applied simultaneously.

According to the present invention, the yield of a necessary part selected from seed, fruit, hypocotyl, root and stem can be markedly enhanced by applying the invention during the time when the harvesting part of a crop becomes enlarged.

DETAILED DESCRIPTION OF THE INVENTION

One of the active ingredients in the yield enhancing agent of the present invention is 5-aminolevulic acid, a derivative thereof (the formula (1)) or a salt of the acid or the derivative.

In the formula (1), the alkyl group represented by $R^1$ and $R^2$ is preferably a linear or branched alkyl group having 1 to 24 carbon atoms, more preferably an alkyl group having 1 to 18 carbon atoms, and particularly preferably an alkyl group having 1 to 6 carbon atoms. Examples of the alkyl group having 1 to 6 carbon atoms include a methyl group, an ethyl group, an n-propyl group, an isopropyl group, an n-butyl group, a sec-butyl group, and the like. The acyl group is preferably a linear or branched alkanoyl group, alkenylcarbonyl group or aroyl group, each of which has 1 to 12 carbon atoms, and particularly preferably an alkanoyl group having 1 to 6 carbon atoms. Examples of the acyl group include a formyl group, an acetyl group, a propionyl group, a butyryl group, and the like. The alkoxycarbonyl group is preferably an alkoxycarbonyl group having 2 to 13 carbon atoms in total, and particularly preferably an alkoxycarbonyl group having 2 to 7 carbon atoms. Examples of the alkoxycarbonyl group include a methoxycarbonyl group, an ethoxycarbonyl group, a n-propoxycarbonyl group, an isopropoxycarbonyl group, and the like. The aryl group is preferably an aryl group having 6 to 16 carbon atoms, and examples thereof include a phenyl group, a naphthyl group, and the like. The aralkyl group is preferably a group formed from an aryl group having 6 to 16 carbon atoms and an alkyl group having 1 to 6 carbon atoms, and examples thereof include a benzyl group and the like.

The alkoxy group represented by $R^3$ is preferably a linear or branched alkoxy group having 1 to 24 carbon atoms, more preferably an alkoxy group having 1 to 16 carbon atoms, and particularly preferably an alkoxy group having 1 to 12 carbon atoms. Examples of the alkoxy group include a methoxy group, an ethoxy group, an n-propoxy group, an isopropoxy group, an n-butoxy group, a pentyloxy group, a hexyloxy group, an octyloxy group, a decyloxy group, a dodecyloxy group, and the like. The acyloxy group is preferably a linear or branched alkanoyloxy group having 1 to 12 carbon atoms, and particularly preferably an alkanoyloxy group having 1 to 6 carbon atoms. Examples of the acyloxy group include an acetoxy group, a propionyloxy group, a butyryloxy group, and the like. The alkoxycarbonyloxy group is preferably an alkoxycarbonyloxy group having 2 to 13 carbon atoms in total, and particularly preferably an alkoxycarbonyloxy group having 2 to 7 carbon atoms in total. Examples of the alkoxycarbonyloxy group include a methoxycarbonyloxy group, an ethoxycarbonyloxy group, an n-propoxycarbonyloxy group, an isopropoxycarbonyloxy group, and the like.

The aryloxy group is preferably an aryloxy group having 6 to 16 carbon atoms, and examples thereof include a phenoxy group, a naphthyloxy group, and the like. The aralkyloxy group preferably has the aralkyl group, and examples thereof include a benzyloxy group, and the like.

In the formula (1), $R^1$ and $R^2$ are each preferably a hydrogen atom. $R^3$ is preferably a hydroxyl group, an alkoxy group or an aralkyloxy group, more preferably a hydroxy group or an alkoxy group having 1 to 12 carbon atoms, and particularly preferably a methoxy group or a hexyloxy group.

The 5-aminolevulic acid derivative may be 5-aminolevulic acid methyl ester, 5-aminolevulic acid ethyl ester, 5-aminolevulic acid propyl ester, 5-aminolevulic acid butyl ester, 5-aminolevulic acid pentyl ester, 5-aminolevulic acid hexyl ester, or the like, and particularly, 5-aminolevulic acid methyl ester or 5-aminolevulic acid hexyl ester is preferred.

Examples of the salts of 5-aminolevulic acid and a derivative thereof include acid addition salts such as hydrochloride, phosphate, nitrate, sulfate, sulfonate, acetate, propionate, butyrate, valerate, citrate, fumarate, maleate and malate; and metal salts such as sodium salt, potassium salt and calcium salt. Among these, hydrochloride, phosphate, nitrate and sulfonate are preferred, and hydrochloride and phosphate are particularly preferred. 5-Aminolevulic acid and derivatives thereof, and salts thereof can be used singly or as mixtures of two or more kinds.

5-Aminolevulic acid, a derivative thereof, or a salt of the acid or the derivative can be produced by any method of chemical synthesis, production by microorganism and production by enzyme. The product can be used without separation and purification, as long as the product does not contain any harmful substances for crops. If the product contains harmful substances, the product can be used after eliminating the harmful substances to an appropriate level which is not considered harmful.

Furthermore, examples of the gibberellin biosynthesis inhibitor, which is one of the active ingredients in the yield enhancing agent of the present invention, include inabenfide (4'-chloro-2'-α-hydroxybenzyl)isonicotinanilide), uniconazole P ((E)-(S)-1-(4-chlorophenyl)-4,4-dimethyl-2-(1H-1,2,4-triazol-1-yl)pent-1-en-3-ol), trinexapac-ethyl (ethyl=4-cyclopropyl-α-hydroxymethylene)-3,5-dioxocyclohexane carboxylate), paclobutrazole ((2RS,3RS)-1-(4-chlorophenyl)-4,4-dimethyl-2-(1H-1,2,4-triazol-1-yl)pentan-3-ol), prohexadione calcium salt (calcium 3-oxido-5-oxo-4-propionyl-3-cyclohexene carboxylate), flurprimidol (2-methyl -pyrimidin-5-yl-1-(4-trifluoromethoxyphenyl)propan-1-ol), ancymidol (α-cyclopropyl-α(4-methoxyphenyl)-5-pyrimidinemethanol), chlormequat (2-chloroethyltrimethylammonium=chloride), and daminozide (N-(dimethylamino)succinamide acid). The inhibitor is preferably inabenfide, uniconazole P, trinexapac-ethyl, paclobutrazole, prohexadione calcium salt or flurprimidol, and is particularly preferably uniconazole P or prohexadione calcium salt.

The yield enhancing agent of the present invention may be used by mixing 5-aminolevulic acid, a derivative thereof or a salt of the acid or the derivative, with an gibberellin biosynthesis inhibitor, but in addition to these, a plant growth regulator, sugars, amino acids, organic acids, alcohols, vitamins, minerals and the like can be used in combination. Examples of the plant growth regulator as used herein include brassinolides such as epibrassinolide; choline agents such as choline chloride and choline nitrate; indole butyrate, indole acetate, an ethychlozate agent, a 1-naphthylacetamide agent, an isoprothiolane agent, a nicotinic acid amide agent, a hydroxyisoxazole agent, a calcium peroxide agent, a benzylaminopurine agent, a metasulfocarb agent, an oxyethylenedocosanol agent, an ethephone agent, a chroquinefonac agent, gibberellin, a streptomycin agent, a daminozide agent, a benzylaminopurine agent, a 4-CPA agent, an ancymidol agent, an inabenfide agent, a uniconazole agent, chlormequat agent, a dikegulac agent, mefluidide agent, a calcium carbonate agent, a piperonyl butoxide agent, and the like.

Examples of the sugars include glucose, sucrose, xylitol, sorbitol, galactose, xylose, mannose, arabinose, majurose, sucrose, ribose, rhamnose, fructose, maltose, lactose, maltotriose, and the like.

Examples of the amino acids include asparagin, glutamine, histidine, thyrosine, glycine, arginine, alanine, tryptophan, methionine, valine, proline, leucine, lysine, isoleucine, and the like.

Examples of the organic acids include formic acid, acetic acid, propionic acid, butyric acid, valeric acid, oxalic acid, phthalic acid, benzoic acid, lactic acid, citric acid, tartaric acid, malonic acid, malic acid, succinic acid, glycolic acid, glutamic acid, aspartic acid, maleic acid, caproic acid, caprylic acid, myristic acid, stearic acid, palmitic acid, pyruvic acid, α-ketoglutamic acid, levulic acid, and the like.

Examples of the alcohols include methanol, ethanol, propanol, butanol, pentanol, hexanol, glycerol, and the like.

Examples of the vitamins include nicotinic acid amide, vitamin $B_6$, vitamin $B_{12}$, vitamin $B_5$, vitamin C, vitamin $B_{13}$, vitamin $B_1$, vitamin $B_3$, vitamin $B_2$, vitamin $K_3$, vitamin A, vitamin $D_2$, vitamin $D_3$, vitamin $K_1$, α-tocopherol, β-tocopherol, γ-tocopherol, σ-tocophero, p-hydroxybenzoic acid, biotin, folic acid, nicotinic acid, pantothenic acid, α-ribonic acid, and the like.

Examples of the minerals include nitrogen, phosphorus, potassium, calcium, boron, manganese, magnesium, zinc, copper, iron, molybdenum, and the like.

The plant (crop) that is the subject of application of the yield enhancing agent of the present invention is not particularly limited, but the plant is preferably a Gramineae, a Cruciferae, a Compositae, an Umbelliferae, a Solanaceae, a Cucurbitaceae, a Chenopodiaceae, a Rosaceae, a Liliaceae or a Malvaceae, and more preferably a Gramineae, a Cruciferae or a Compositae, and is a crop which enlarges in the seed, fruit, hypocotyl, stem and root.

Examples of the Gramineae include rice, wheat, barley, maize, sorghum, and the like, and examples of the Cruciferae include daikon radish, radish, turnip, and the like. Examples of the Compositae include sunflower, burdock, and the like, and examples of the Umbelliferae include carrot and the like. Examples of the Solanaceae include eggplant, tomato, bell pepper, sweet potato, chili, and the like, and examples of the Cucurbitaceae include cucumber, pumpkin, watermelon, melon, and the like. Examples of the Chenopodiaceae include sugar beet, and examples of the Rosaceae include strawberry. Examples of the Liliaceae include onion, and examples of the Malvaceae include okra, cotton, and the like.

The plant is most preferably rice, barley, radish and sunflower.

The subject of yield enhancement for the yield enhancing agent of the present invention is the harvesting part of a crop, and specifically the seed, fruit, hypocotyl, root or stem. The harvesting part varies with the crop as the subject.

As the time of applying the yield enhancing agent of the present invention to crops, it is preferable to apply during the time when the harvesting part of the subject crop becomes enlarged, and it is more preferably a time period of 14 days before and after flowering or ear emergence when vegetative growth changes to generative growth, or a time period of from 3 days before the enlargement of the target harvesting part to the completion of enlargement. The time is more preferably a time period of 10 days before and after flowering or ear emergence when vegetative growth changes to generative growth, or 14 days starting from the initiation of enlargement of the target harvesting part. However, the time may vary with the various crops, and is not limited to this.

Specifically, for example, concerning rice, the time is preferably 14 days before and after ear emergence, and more preferably from the initiation of ear emergence to 7 days thereafter.

Concerning barley, the time is preferably 14 days before and after ear emergence, and more preferably from 7 days before the initiation of ear emergence to the initiation of ear emergence.

Concerning radish, the time is preferably from 3 days before the initiation of hypocotyl enlargement to the completion of enlargement, and more preferably from the day of initiation of hypocotyl enlargement to 14 days thereafter.

Concerning sunflower, the time is preferably 14 days before and after flowering, and more preferably from the day of flowering to 10 days thereafter.

The yield enhancing agent of the present invention is used by administering to the roots, stems and leaves of the crop, or to the soil and water in the surroundings. The form at the time of administration may be solid or may be an aqueous solution. Specifically, the yield enhancing agent may be used for foliage treatment (foliage treating agent), or may be used for soil treatment (soil treating agent). Furthermore, the agent may also be subjected to absorption before planting, cuttage or the like. The agent may also be added to water upon hydroponic culture.

In regard to 5-aminolevulic acid, a derivative thereof or a salt of the acid or the derivative and the gibberellin biosynthesis inhibitor, which are the active ingredients of the yield enhancing agent of the present invention, the gibberellin biosynthesis inhibitor may be used in an amount of 10 to 50000 parts by weight, preferably 50 to 10000 parts by weight, and particularly preferably 100 to 5000 parts by weight, with respect to 100 parts by weight of 5-aminolevulic acid, a derivative thereof or a salt of the acid or the derivative. However, the weight ratio varies with the gibberellin biosynthesis inhibitor used.

Specifically, in regard to the administration of the yield enhancing agent to crops, it is preferable to use the yield enhancing agent in an amount of 0.1 to 10000 mg, particularly preferably 1 to 2000 mg, and more preferably 1 to 1000 mg, per 10 ares in terms of 5-aminolevulic acid, a derivative thereof or a salt of the acid or the derivative. The treatment amount of uniconazole P as the gibberellin biosynthesis inhibitor is preferably 0.1 to 10 g, and more preferably 0.2 to 1 g, per 10 ares, while the treatment amount of prohexadione calcium salt is preferably 0.1 to 20 g, and more preferably 0.2 to 10 g, per 10 ares. It is preferable to treat with 10 to 1000 L, and more preferably 20 to 300 L, per 10 ares of an agent in which the treatment amount has been adjusted to in the range described above.

In the case of using the yield enhancing agent as a foliage treating agent, the type and amount of use of the spreading agent is not particularly limited.

The 5-aminolevulic acid, a derivative thereof or a salt of the acid or the derivative and the gibberellin biosynthesis inhibitor, which are the active ingredients of the yield enhancing agent of the present invention, can be simultaneously used in the treatment, or may be used in the treatment at different times.

The two components of 5-aminolevulic acid, a derivative thereof or a salt of the acid or the derivative and the gibberellin biosynthesis inhibitor, which are the active ingredients of the yield enhancing agent of the present invention, are preferably simultaneously used to treat, but when the respective components are used to treat at different times, it is preferable to first perform a treatment with one component and then perform a treatment with the remaining one component within 14 days, and it is more preferable to perform a treatment with the remaining one component within 10 days. Furthermore, the number of performances of the treatment with 5-aminolevulic acid, a derivative thereof or a salt of the acid or the derivative during the growth of crops is not limited, and the treatment can be performed multiple times at every 7 to 14 days. Thus, since the growing period varies with the crop, multiple treatments can be performed for crops which grow over a long time.

EXAMPLES

Hereinafter, the present invention will be described in detail with reference to Examples, but these are only for the illustrative purposes, and the present invention is not to be limited to these Examples.

Example 1

Effect of Enhancing Yield of Rice

Seeds of rice (variety: Koshihikari) were sterilized with 70% ethanol, and rice seeds heavier than a specific gravity of 1.13 were screened by brine washing. Water absorption for one night at 30° C. and germination for one night were carried out, and then the seeds were sowed in a seedling box (4/11). A certain amount of kuroboku soil was placed in a 15-L Polybucket (1/17500×10 a), a synthetic fertilizer was mixed therein as a basal fertilizer such that N-P-K=5-5-5 kg/10 a, and water was drawn in to a water depth of 3 cm. Grown seedlings were planted at 3 stocks per bucket (5/15). Three days after ear emergence (8/11), prohexadione calcium salt was used as an gibberellin biosynthesis inhibitor to treat at 0.4 g.a.i./10 a (100 L/10 a) (8/14). Furthermore, 5-aminolevulic acid (ALA) hydrochloride was used for a foliage treatment for three times (8/14, 8/30, 9/10) at 0.1 g.a.i/10 a (100 L/10 a). Four buckets were used for one test zone, and the buckets were placed randomly so as not to be affected by the place. After harvesting (9/21), the number of ears per stock, the number of rice grains per ear, ripening rate (number of rice grains having a specific gravity of 1.06 or more/number of total rice grains×100), and the weight of one thousand grains were measured, and the respective values were multiplied to determine the yield of rice per stock. The results are presented in Table 1.

TABLE 1

| | Rice yield | | | | |
|---|---|---|---|---|---|
| | Ripening rate | Weight of thousand grains (g) | Number of rice grains per ear | Number of ears per stock | Yield of rice per stock (g) |
| Untreated | 85.83 | 22.57 | 80.4 | 20.1 | 31.3 |
| ALA hydrochloride 0.1 g/10 a | 88.71 | 21.9 | 80.12 | 20.2 | 31.4 |
| Prohexadione calcium salt 0.4 g/10 a | 86.09 | 22.22 | 80.35 | 20.2 | 31.0 |
| ALA hydrochloride 0.1 g/10 a + prohexadione calcium salt 0.4 g/10 a | 91.22 | 23.71 | 80.45 | 20.0 | 34.8 |

As shown in Table 1, it was found that when 5-aminolevulic acid hydrochloride and prohexadione calcium salt are combined, the yield of rice grains per stock of paddy is enhanced.

Example 2

Effect of Enhancing Yield of Barley Grains

A certain amount of kuroboku soil was placed in a 15-L Polybucket (1/17500×10 a), a liquid fertilizer Hyponica was applied as a basal fertilizer such that N-P-K=5.0-2.8-8.5 kg/10 a, and barley was sowed (11/3). Five stocks of seedlings were planted per bucket, and in the middle of growth, thinning was performed to make the test zone uniform so that there would be 3 stocks per bucket. Five days before ear emergence (4/15), prohexadione calcium salt was used as an gibberellin biosynthesis inhibitor to treat at 7.0, 3.5 g.a.i./10 a (150 L/10 a) (4/10). Furthermore, a treatment with 5-aminolevulic acid hydrochloride was performed at 0.15 g.a.i/10 a (150 L/10 a) under the conditions of performing a foliage treatment each time at the respective times of before (4/3), simultaneously with (4/10) and after (5/8) the treatment with prohexadione calcium salt. As additional fertilization, a liquid fertilizer Hyponica was applied such that N-P-K=3.0-1.7-5.1 kg/10 a (4/14, 5/8). After harvesting (6/11), the weight of barley grains per stock was examined. Four buckets were used per test zone. The results are presented in Table 2.

TABLE 2

| | Barley yield Weight of grains per stock (g) | | | | |
|---|---|---|---|---|---|
| | | | ALA hydrochloride | | |
| | | None | 7 days before prohexadione calcium salt treatment | Simultaneous with prohexadione calcium salt treatment | 28 days after prohexadione calcium salt treatment |
| Prohexadione calcium salt | None | 6.07 | 6.59 | 6.83 | 6.45 |
| | 7 g.a.i/10 a | 6.60 | 6.69 | | 6.72 |
| | 3.5 g.a.i/10 a | 6.23 | 7.01 | 7.13 | 7.33 |

As shown in Table 2, it was found that when 5-aminolevulic acid hydrochloride and prohexadione calcium salt are combined, the yield of barley grains per stock of barley is enhanced.

Example 3

Verification of Effect of Enhancing Yield of Radish Hypocotyl

A certain amount of kuroboku soil was placed in a No. 6 pot (1/75000×10 a), and radish (variety: Red Chime) was planted (5/4). A liquid fertilizer Hyponica was applied as a basal fertilizer such that N-P-K=5.0-2.8-8.5 kg/10 a (5/8). Five stocks were planted per pot, and in the middle of growth, thinning was performed to make the test zone uniform so that there would be 3 stocks per pot. Ten days after the initiation of hypocotyl enlargement, prohexadione calcium salt was used as an gibberellin biosynthesis inhibitor to treat at 15 g.a.i./10 a (150 L/10 a) (5/27). Furthermore, a treatment with 5-aminolevulic acid hydrochloride was performed at 0.1 g.a.i/10 a (150 L/10 a) under the conditions of performing a foliage treatment (6/2) six days after the treatment with prohexadione calcium salt. As additional fertilization, a liquid fertilizer Hyponica was applied such that N-P-K=3.0-1.7-5.1 kg/10 a (5/29). After harvesting (6/7), the fresh weight of hypocotyl was measured. Seven pots were used per test zone. The results are presented in Table 3.

TABLE 3

Radish hypocotyl yield

| | Fresh weight of hypocotyl (g) |
|---|---|
| Untreated | 11.6 |
| ALA hydrochloride treatment 0.1 g/10a | 12.2 |
| Prohexadione calcium salt treatment 15 g/10a | 10.3 |
| ALA hydrochloride 0.1 g/10a + prohexadione calcium salt treatment 15 g/10a | 13.0 |

As shown in Table 3, it was found that when 5-aminolevulic acid hydrochloride and prohexadione calcium salt are combined, the average hypocotyl weight of radish is enhanced, and the yield is enhanced.

Example 4

Verification of Effect of Enhancing Yield of Sunflower Seeds

A test field (red soil) was divided into 0.7 m² per compartment, and sunflower (variety: Hybrid Sunflower) was planted (6/9). A synthetic fertilizer was applied as a basal fertilizer such that N-P-K=5.0-5.0-5.0 kg/10 a (6/9). Four stocks were planted per test zone, and in the middle of growth, thinning was performed to make the test zone uniform so that there would be two stocks per test zone. Seven days after flowering, a Sumiseven P liquid preparation (containing 0.025% of uniconazole P) as an gibberellin biosynthesis inhibitor was used for treatment such that the amount of treatment of uniconazole P would be 0.3 g.a.i/10 a (300 L/10 a) (8/20). Furthermore, a foliage treatment with 5-aminolevulic acid hydrochloride was performed at 0.2 g.a.i/10 a (300 L/10 a), two times in total at the date of uniconazole P treatment (8/20) and 2 weeks after the uniconazole P treatment (9/3). As additional fertilization, a synthetic fertilizer was applied such that N-P-K=3.0-3.0-3.0 kg/10 a (7/8). After harvesting (9/16), the number and weight of seeds of each plant body were measured. This time, empty seeds without kernels were excluded. The test zone was provided as 6 test zones under each condition.

TABLE 4

Sunflower seed yield

| | Weight of filled seeds (g/stock) | Number of filled seeds (seeds/stock) | Live weight of plant body (kg/stock) |
|---|---|---|---|
| Untreated | 126.4 | 1357 | 1.81 |
| ALA hydrochloride 0.2 g/10a | 120.5 | 1348 | 1.68 |
| Uniconazole P 0.3 g/10a | 126.3 | 1377 | 1.96 |
| ALA hydrochloride 0.2 g/10a + uniconazole P 0.3 g/10a | 136.0 | 1533 | 1.90 |

As shown in Table 4, it was found that when 5-aminolevulic acid hydrochloride and Uniconazole P are combined, the yield of sunflower seeds is enhanced.

Furthermore, this time, the weight of the sunflower plant body did not change. In a previously reported document where it is characterized by treating sugar beet young seedlings with 5-aminolevulic acid and uniconazole, the effect involved recovering the growth stagnation of plant by uniconazole by 5-aminolevulic acid that is used in combination, or further enhancing the dry weight of the plant body, but it is known that in the case of performing the treatment before and after flowering, there was no influence exerted to the growth of the plant body itself.

Comparative Example

Effect of Combined Treatment of 5-Aminolevulic Acid Hydrochloride and Gibberellin Biosynthesis Inhibitor During Seedling Growth on Yield Turnip (variety: Honami) was sowed (9/11) in a Jiffy pot, and plant settling was carried out (9/24) in a test field (red soil) that had been divided into 0.4 m² per compartment. At this time, a synthetic fertilizer was applied as a basal fertilizer such that N-P-K=5-5-5 kg/10 a. Four stocks were planted per test zone, and 4 test zones were set up randomly for one condition so as not to be affected by the place. Seven days before the initiation of enlargement which was the time when the seedlings after plant settling were growing, a treatment was performed with prohexadione calcium salt as an gibberellin biosynthesis inhibitor in an amount of treatment of 20 g.a.i/10 a (200 L/10 a) and with 5-aminolevulic acid hydrochloride in an amount of treatment of 0.2 g.a.i/10 a (200 L/10 a) (10/16). After harvesting (11/12), the weights of the aerial part and the terrestrial part of the plant body were measured.

TABLE 5

| | Turnip yield | |
|---|---|---|
| | Weight of aerial part (kg/stock) | Weight of terrestrial part (kg/stock) |
| Untreated | 0.344 | 0.644 |
| ALA hydrochloride 0.2 g/10a | 0.368 | 0.725 |
| Prohexadione calcium salt 20 g/10a | 0.349 | 0.641 |
| ALA hydrochloride 0.2 g/10a + prohexadione calcium salt 20 g/10a | 0.364 | 0.675 |

When 5-aminolevulic acid hydrochloride and prohexadione calcium salt were combined upon the growth of seedlings, turion was prevented, and healthy growth of seedlings was observed. Furthermore, in the treatment with 5-aminolevulic acid hydrochloride and the treatment of combining 5-aminolevulic acid hydrochloride and prohexadione calcium salt, the effect in terms of healthy growth of seedlings was observed to be the same. Here, as shown in Table 5, in the treatment of combining 5-aminolevulic acid hydrochloride and prohexadione calcium salt with respect to the treatment with 5-aminolevulic acid, even when the weights of the aerial part and the terrestrial part after the roots had been eventually enlarged were compared, an enhancement of the yield could not be seen.

From this result, it is understood that during the time for the growth of seedlings, the yield is not enhanced even if a treatment is carried out by combining 5-aminolevulic acid hydrochloride and an gibberellin biosynthesis inhibitor.

This application claims priority from Japanese Patent Application No. 2009-057313 filed on Mar. 11, 2009, the entire subject matter of which is incorporated herein by reference.

What is claimed is:

1. A method for enhancing a yield of a seed of a crop to be harvested, wherein the crop to be harvested is a Gramineae or a Compositae, wherein the method comprises applying 5-aminolevulic acid or a salt thereof and at least one gibberellin biosynthesis inhibitor selected from the group consisting of uniconazole P, prohexadione calcium salt, and salts or isomers thereof fourteen days before and after flowering or ear emergence or from three days before enlargement of the part of the crop to be harvested to completion of the enlargement,
wherein the amount of gibberellin biosynthesis inhibitor is present in an amount of 10 to 5000 parts by weight with respect to 100 parts by weight of 5-aminolevulinic acid or a salt of the acid.

2. The method for enhancing a yield according to claim 1, wherein the 5-aminolevulinic acid or a salt thereof and the gibberellin biosynthesis inhibitor are applied simultaneously.

3. The yield enhancing combination according to claim 1, wherein the crop of Gramineae, or Compositae is rice, barley or sunflower.

* * * * *